United States Patent

Coupland et al.

[11] Patent Number: 5,859,264
[45] Date of Patent: Jan. 12, 1999

[54] EXPLOSIVE COMPOSITIONS

[75] Inventors: Keith Coupland, Hotham; Barry Love, Beverly, both of Great Britain

[73] Assignee: Croda International, PLC, United Kingdom

[21] Appl. No.: 737,508

[22] PCT Filed: Mar. 11, 1996

[86] PCT No.: PCT/GB96/00565

§ 371 Date: Feb. 12, 1997

§ 102(e) Date: Feb. 12, 1997

[87] PCT Pub. No.: WO96/28436

PCT Pub. Date: Sep. 19, 1996

[30] Foreign Application Priority Data

Mar. 13, 1995 [GB] United Kingdom ............... 9505028

[51] Int. Cl.⁶ .................................. C07D 319/06
[52] U.S. Cl. .......................................... 549/372
[58] Field of Search ............................. 549/372

[56] References Cited

U.S. PATENT DOCUMENTS

| | | | |
|---|---|---|---|
| H253 | 4/1987 | Sitzmann et al. | 549/321 |
| 3,155,685 | 11/1964 | Prill et al. | 260/343.5 |
| 3,155,686 | 11/1964 | Prill et al. | 260/343.5 |
| 3,248,187 | 4/1966 | Bell, Jr. | 260/343.5 |
| 3,261,782 | 7/1966 | Anderson et al. | 260/343.6 |
| 3,487,452 | 12/1969 | Wygant et al. | 260/343.6 |
| 3,897,350 | 7/1975 | Heiba et al. | 252/334 |
| 3,925,232 | 12/1975 | Heiba et al. | 252/171 |
| 4,190,588 | 2/1980 | Heiba et al. | 252/544 |
| 4,221,720 | 9/1980 | Brois et al. | 260/343.6 |
| 5,183,908 | 2/1993 | Elsasser et al. | 549/322 |

FOREIGN PATENT DOCUMENTS 0331306  2/1989  European Pat. Off. .
3102353  1/1982  Germany .

OTHER PUBLICATIONS

Sitzmann et al, Chemical Abstract vol. 107 No. 25,638 "Energetic banded drain polynitrodial synthesis" 1987.

Showa et al, Chemical abstract vol. 101 No. 74, 422 "Emulsion polymsization" 1982.

*Primary Examiner*—John Kight
*Assistant Examiner*—Raymond Covington
*Attorney, Agent, or Firm*—Stevens, Davis, Miller & Mosher, L.L.P.

[57] ABSTRACT

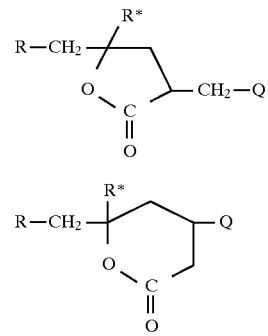

Gamma and delta lactones of formulae (I and 11) are used as emulsifiers in explosive compositions comprising a continuous organic phase and a discontinuous aqueous phase containing an oxygen-supplying compound. In the formulae, R is hydrocarbyl, R* is hydrogen, methyl or another hydrocarbyl, and Q is an amide, ammonium salt or ester functionality.

12 Claims, No Drawings

EXPLOSIVE COMPOSITIONS

This invention relates to explosive compositions and, more particularly, to certain emulsifiers therefor and to their preparation.

It is known to make explosive compositions as water-in-oil emulsions in which the discontinuous aqueous phase contains the oxygen-releasing compound. To stabilise these emulsions, an emulsifier is used, and examples are given in EP-A-0155800, EP-A-0285608 and GB-A-2187182. Among these proposed emulsifiers are compounds of poly[alk(en)yl] succinic acid or anhydride, such as salts or amides thereof.

We have now found a particular group of compounds, which can be made from poly[alk(en)yl] succinic acid, which are especially useful as emulsifiers for explosive compositions. In particular, these emulsifiers provide surprisingly good emulsion stability which is, of course, an important desideratum in explosive compositions.

According to one aspect of the present invention, we have found that lactones of the formulae I and II are very effective emulsifiers in explosive compositions. These lactones are the γ-lactone of formula I:

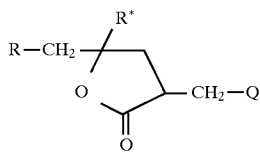

and the δ-lactone of formula:

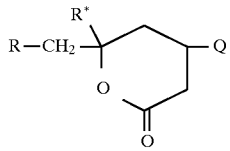

wherein R is a hydrocarbyl group, and R* may be hydrogen or methyl or another hydrocarbyl group.

R can vary widely but preferably it is a saturated poly(alkylene) group where the alkylene part has from 2 to 6 carbon atoms, and most especially a saturated polyisobutylene group of the formula:

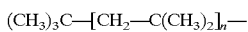

where n is from about 5 to about 120, most preferably from about 10 to 60.

The group Q may be:

1. an amide functionality. where Q is of the formula

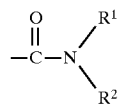

where $R^1$ is hydrogen or an alkyl, cycloalkyl or aryl group which may optionally be substituted; and $R^2$ is hydrogen or an alkyl, cycloalkyl or aryl group which may optionally be substituted.

2. an ammonium salt of a carboxylic acid, where Q is of the formula

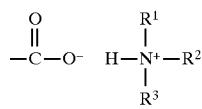

where $R^1$ and $R^2$ are as defined above and $R^3$ is hydrogen or an alkyl, cycloalkyl or aryl group which may optionally be substituted.

3. an ester functionality, where Q is Of the formula

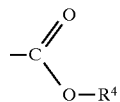

where $R^4$ is a hydrocarbyl or substituted hydrocarbyl group derived from an alcohol, monomeric polyol or oligomeric poly(oxyalkylene) or alkanolamine grouping.

In one aspect, therefore, the invention provides the use of a lactone as defined above as an emulsifier in an explosive composition.

The invention also includes an explosive composition comprising an emulsion having an organic, preferably hydrocarbon, continuous phase and a discontinuous aqueous phase containing an oxygen-supplying compound, usually ammonium nitrate, and a lactone emulsifier of the invention.

By way of example, the organic continuous phase can be selected from fuel oil, diesel oil, kerosene, naptha, paraffin oils, waxes, animal oils, fish oils, methyl and/or ethyl esters of fatty acids (so called biodiesels) and other mineral, hydrocarbon or fatty oils, and any mixtures of two or more thereof. The preferred organic continuous phase components are liquid hydrocarbons such as diesel, gasoline, kerosene, fuel oils and paraffin oils.

The oxygen-supplying compound can be, for example, alkali and alkaline earth metal nitrates, chlorates and perchlorates; ammonium nitrate, chlorates and perchlorates; and any mixture of two or more thereof. The preferred oxygen-supplying compounds include ammonium nitrate, sodium nitrate and calcium nitrate and most preferably ammonium nitrate or a mixture of ammonium nitrate and sodium or calcium nitrate.

The relative amounts of constituents of these explosive compositions can vary widely but will generally be:

(a) organic phase: 2% to 15%, preferably 3% to 10%.
(b) aqueous phase: 85% to 98%, preferably 90% to 97%.
(c) oxygen-containing compound: 40% to 95% , preferably 60% to 90%.
(d) emulsifier: up to 5%, preferably 0.1%, to 2.0%.

Percentages are by weight of the composition.

It is also possible to incorporate other additives in the emulsions of the invention in order to improve sensitivity, density, strength, rheology and other desirable aspects of the final emulsion explosives. The type and quantity of such additives will vary according to the effect desired and will be determined by those skilled in the art.

By way of example, sensitizing components may be occluded gas bubbles such as glass or resin microspheres or other gas-containing particulate materials. Gas bubbles may also be generated in-situ by the incorporation and distribution of a gas generating material such as sodium nitrite solution. Self-explosive sensitizers such as TNT and amine nitrates may also be employed. Such sensitizing agents may be used alone or in combination and are distributed homogeneously throughout the emulsion matrix.

By further example, secondary fuels such as finely divided aluminum or sulphur may also be included.

The emulsions of the invention may also be blended with particulate oxygen supplying salts such as prilled ammonium nitrate, or prilled ammonium nitrate/fuel oil ("ANFO") blends, in various ratios, to produce so called "Heavy Anfo" explosives.

The lactone emulsifiers of the present invention can be made, in accordance with a further aspect of the invention, by reacting a γ-lactone acid of formula:

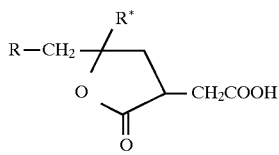
VII or a δ-lactone acid formula:

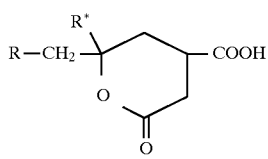
VIII with an amine of formula $R^1R^2R^3N$ where R, R*, $R^1$, $R^2$ and $R^3$ are as defined above. Depending on the reaction conditions employed, the resultant product may contain the group Q as either an amide functionality (IV) or salt functionality (V) or as a mixture of the two types.

$R^1$, $R^2$ and $R^3$ may vary widely. Among the preferred amines and substituted amine reagents are 3-dimethylaminopropylamine, tetraethylenepentamine, diethylenetriamine, 3-diethylaminopropylamine, N,N-diethylethylenediamine, 4-(2-aminoethyl)morpholine, 1-(2-aminoethyl)piperazine, 2-(methylamino)ethanol, 2-amino-2-ethyl-1,3-propanediol, ethanolamine, diethanolamine and triethanolamine.

There are other possibilities, as will be clear to those skilled in the art.

The lactone emulsifiers of the present invention may also be made by reacting γ- and δ-lactone acids (VII and VIII) with alcohols, monomeric polyols or oligomeric poly (oxyalkylene) groups so that the resultant product contains an ester functionality in the group Q (VI). $R^4$ may vary widely and among the preferred reagents resulting in such ester functionalities are ethylene glycol, (polyethylene glycol), glycerol, diglycerin, sorbitol and triethanolamine.

Other possibilities will be apparent to those skilled in the art. The lactonisation is effected under acid catalysis.

It will be appreciated that where the γ- and δ-lactone acids (VII and VIII) are reacted with reagents containing more than one functional group (for example triethanolamine), then the reaction product may contain a mixture of derivatives whereby individual derivatives will contain either an ester or salt functionality in the group Q.

In a further embodiment of the present invention. the different emulsifiers of the invention may be blended together and/or with other emulsifiers known in the art for their utility as emulsifiers for explosive compositions.

As is known the γ- and δ-lactone acids can be made by protonising a polyalk(en)yldiacid of formula:

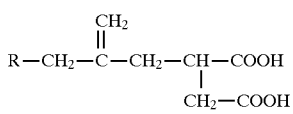
IV or

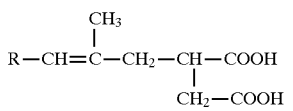
X and then lactonising. The principal product (90 to 95%) is the γ-lactone acid of formula VII but there is also formed a small amount (up to about 10%) of the δ-lactone acid of formula VIII.

The γ- and δ-lactone acids VII and VIII can be separated at this stage so that subsequent reaction to provide the functionality Q provides an emulsifier of the invention. However, there is no particular advantage in separating the acids, and the mixture can be further reacted to provide a mixture of emulsifiers of the invention. This mixture can be used as is, or it can be separated into its constituents, as will be clear to those skilled in the art.

It will be appreciated that the emulsifiers of the invention contain chiral centres and thus can give rise to isomeric products.

In order that the invention may be more fully understood, the following Examples are given by way of illustration only:

EXAMPLE 1

Preparation of acid lactones

The compound n-octenylsuccinic anhydride is subjected to acid hydrolysis and lactonisation.

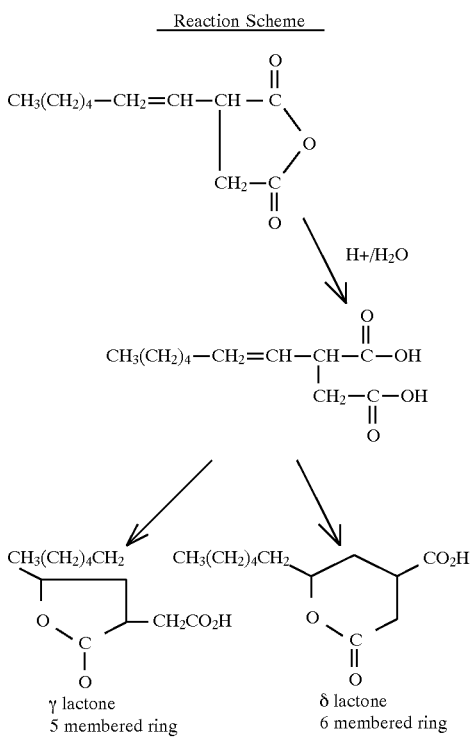

A mixture of n-octenylsuccinic anhydride (210g, 1.0 mol) and water (20 g, 1.1 mol) was heated with stirring for 30 minutes at 100°–110° C. Concentrated sulphuric acid (5 drops) was added and the reaction mixture was stirred for 16 hours at 155° C. A dark brown product was obtained.

The mixture was allowed to cool to room temperature and a solid precipitate was produced. The solid was filtered off and recrystallised (acetone, 4 times) to give a white crystalline solid, yield (40 g, 18%, m.p. 94° C. The purity was also determined by the tlc (eluant CHCl$_3$, methanol, acetone, acetic acid 50:35:13:3 Rf (0.78)).

I.r. (nujol Moll) max 3400–2400 (COOH), 2950, 2920, 2850, 1755 (C=O-lactone), 1735 (Shoulder C=O-lactone), 1700 (C—OH), 1500–720 (complex region) cm$^{-1}$. M.s. 229 (M+H), 210 (M–H$_2$O). $^1$H.N.m.r. (CDCl$^3$) 0.80–1.00 (3H, m), 1.15–1.50) (8H,m), 1.60–1.95 (3H,m), 2.15–2.35 (m), 2.50–2.75 (2H,m), 2.85–3.10 (2H,m), 4.35–4.50 and 4.55–4.65 (1H,ms ratio 17:1), 11.35–10.55 (1H,s) ppm.

$^{13}$C.N.m.r. (CDCl$^3$) confirms the presence of two isomeric products each with two carbonyls, —CHO— and alkyl chains.

EXAMPLE 2

The lactone acids of Example 1, were reacted with octylamine.

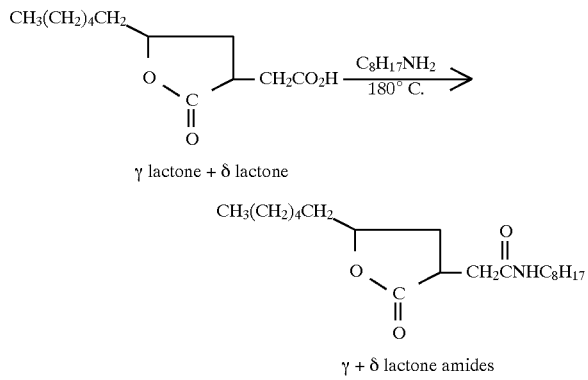

Procedure

A mixture of n-octenylsuccinic acid lactones (m.p. 94° C., 5.075 g, 0.02 mol) and octylamine (2.968 g, 0.023 mol) was heated with stirring to 180° C. for 5 hours. Samples were analysed by tlc (eluant CHCl$_3$, methanol, acetone, acetic acid 50:35:12:3) and I.r. at 1 hourly intervals. The reaction produced a golden yellow oil, crude yield (7.799 g). A sample (2.0255 g) was purified by distillation (Kugelruhr 210° C., 0.1 mm Hg) and gave a colourless distillate (1.8733 g, 92%) which solidified to a waxy solid on cooling to room temperature, m.p. 22°–23° C. The residue from this distillation was 0.1383 g (6.8%). The purity of the product was determined by tlc (eluant CHCl$_3$/methanol 66:33, Rf 0.76).

I.r. (film λmax 3440–3400 (CONH—), 2960, 2930, 2860, 1765 (γ-lactone), 1690, 1650 (—CO—NH—), 1460–1000 (complex region) cm$^{-1}$. M.s. 339 (M), 254 (M–C$_6$H$_{13}$), 211 (M–C$_8$H$_{17}$NH) $^1$H.N.m.r. γ (CDCl$_3$) 0.8–1.0 (6H,m), 1.15–1.40 (16H,m), 1.45–1.80 (5H,m), 1.85–2.10 (1H,m), 2.10–2.80 (3H,m) 2.85–3.15 (2H,m), 3.15–3.30 (m), 3.40–3.55 (2H,m), 3.60–3.75 and 3.80–3.90 (1H,ms), 4.35–4.50 and 4.52–4.62 (m), 5.90–6.05 (1H,m).

EXAMPLE 3

The lactone acids of Example 1, were reacted with 3-diethylaminopropylamine (DEAPA).

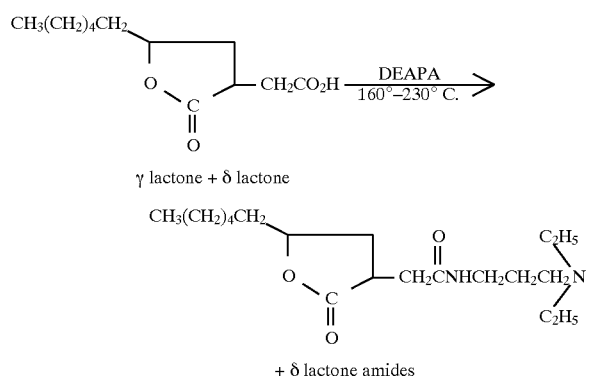

Procedure

A mixture of n-octenylsuccinic acid lactones (m.p. 94° C., 5.012 g, 0.022 mol) and diethylaminopropylamine (DEAPA, 3.037 g, 0.023 mol) was heated with stirring to 160° C. and maintained at this temperature for 2 hours. The temperature was raised to 180° C. and the mixture stirred for 5 hours. The water produced during the reaction was continually distilled off. The reaction produced a light golden oil, crude yield (7.980 g). A sample (1.9943 g) was purified by distillation (Kugelruhr 215° C., 0.1 mm Hg) and gave a pale yellow distillate (1.0830 g (4.16%). The distillate was analysed by tlc (eluant CHCl$_3$, methanol, acetic acid 50:47:3; developing spray—Dragendorff's reagent, Rf 0.24 and 0.16).

I.r. (film) λmax 3400–3380 (CONH—), 2960, 2920, 2860, 2850, 2800, 1765 (γ-lactone C=O), 1690, 1650 (—CH—NH—), 1540, 1460–1000 (Complex region) cm$^{-1}$. M.s. No mass ion given—interpretation difficult. $^1$H.N.m.r. (CDCl$_3$) 0.8–0.92 (3H,t), 0.95–1.10 (6H,m), 1.18–1.38 (8H, m), 1.40–1.55 (2H,m), 1.55–1.85 (3H,m), 1.85–2.02 (1H, m), 2.35–2.60 (7H,m), 2.70–3.15 (3H,m), 3.30–3.40 (m), 3.45–3.60 (2H,m), 3.60–3.72 and 3.75–3.90 (1H,ms), 4.35–4.45 and 4.50–4.60 (ms) ppm.

EXAMPLE 4

In essentially the same way as Examples 1 to 3, the lactone acids of polyisobutenyl succinic acid were reacted with DEAPA to make emulsifiers of the invention as follows A mixture of polyisobutenyl succinic acid (Adibis ADX101B. 6021 g) and distilled water (59.4 g) was heated with stirring to 60° C. Concentrated sulphuric acid (82.5 g) was added and the reaction mixture was stirred and heated to about 100° C. and maintained at this temperature for 1 hour. The reaction was followed by infra-red spectroscopy, which confirmed the formation of polyisobutenyl succinic acid lactones.

Ir (thin film) λmax ≈1765 (C=O γ-lactone), 1735 (shoulder, C=O δ-lactone), 1700 (C=O).

Sodium carbonate (87.5 g) was added to neutralise the mixture which was stirred for a further hour and then allowed to cool to room temperature. A portion of the above reaction mixture (6080 g) was warmed to about 100° C. and DEAPA (716.6 g) was added slowly with stirring under a nitrogen atmosphere. The mixture was heated to about 180° C. and maintained at this temperature for 2 ½ hours before cooling. The resultant reaction mixture contains primarily emulsifiers of the invention where the group Q is believed to be predominantly an amide functionality.

EXAMPLE 5

In a similar manner to Example 4, polyisobutenyl succinic acid lactones were prepared and a portion of the reaction mixture (143.0 g) reacted with diethanolamine (11.0 g) for 3 hours at about 180° C. under a nitrogen atmosphere before cooling.

The resultant mixture contains primarily emulsifiers of the invention where the group Q is believed to be predominantly a substituted amide functionality. The acid value of the product was 2.2 mg KOH g$^{-1}$.

EXAMPLE 6

In a similar manner to Example 4, polyisobutenyl succinic acid lactones were prepared and a portion of the reaction mixture (143.0 g) reacted with 1(2-aminoethyl)piperazine (13,7 g) for 3 hours at 180° C. under a nitrogen atmosphere. The reaction mixture was then allowed to cool to room temperature.

The resultant product contains primarily emulsifiers of the invention where the group Q is believed to be predominantly an amide functionality. The acid value of the product was 1.8 mg KOHg$^{-1}$.

EXAMPLE 7

In a similar manner to Example 4, polyisobutenyl succinic acid lactones were prepared and a portion of the reaction mixture (143.0 g) reacted with diethylenetriamine (15.5 g) for 3 hours at about 180° C. under a nitrogen atmosphere. The reaction mixture was then allowed to cool to room temperature.

The resultant product contains primarily emulsifiers of the invention where the group Q is believed to be predominantly an amide functionality. The acid value of the product was 51.4 mg KOHg$^{-1}$.

EXAMPLE 8

In a similar manner to Example 4, polyisobutenyl succinic acid lactones were prepared and a portion of the reaction mixture (304.3 g) reacted with diethylenetriamine (13.5 g) for 2½ hours at about 180° C. under a nitrogen atmosphere. The reaction mixture was then allowed to cool to room temperature.

The resultant product contains primarily emulsifiers of the invention where the group Q is believed to be predominantly an amide functionality.

EXAMPLE 9

In a modification of the procedures of Example 4, a mixture of polyisobutenyl succinic acid (2000 g) and distilled water (21.4 g) was stirred and heated to about 95° C. until infra-red spectra indicated the formation of the succinic acid derivative (approximately 2½ hours). Concentrated sulphuric acid (21.4 g) was then added and the temperature maintained at about 95° C. until infra-red spectra indicated the formation of lactone species (approximately 2 hours). The mixture was then allowed to cool.

Polyisobutenyl succinic acid lactones (200 g) from the above reaction and ethanolamine (10.5 g) were heated with stirring to about 180° C. under a nitrogen atmosphere for 3 hours. The reaction mixture was then allowed to cool to room temperature.

The resultant product contained primarily emulsifiers of the invention where the group Q was an amide functionality. The acid value of the product was 2.6 mg KOHg$^{-1}$.

EXAMPLE 10

Polyisobutenyl succinic acid lactones from Example 9 (150 g) and ethanolamine (7.9 g) were heated with stirring to about 95° C. under a nitrogen atmosphere for 4½ hours (although infra-red spectra indicated no significant changes occurred after 1 hour). The reaction mixture was then allowed to cool to room temperature.

The resultant product contained primarily emulsifiers of the invention where the group Q was predominantly an ammonium salt. The acid value of the product was 34.1 mg KOHg$^{-1}$.

EXAMPLE 11

Polyisobutenyl succinic acid lactones from Example 9 (200 g) and triethanolamine (26.1 g) were heated with stirring to about 180° C. under a nitrogen atmosphere for 3 hours. The reaction mixture was then allowed to cool to room temperature.

The resultant product had an acid value of 2.9 mg KOHg$^{-1}$.

EXAMPLE 12

Polyisobutenyl succinic acid lactones from Example 9 (150 g) and triethanolamine (19.69) were heated with stirring to about 95° C. under a nitrogen atmosphere for 4½ hours (although infra-red spectra indicated no significant change occurred after 3½ hours). The reaction mixture was then allowed to cool to room temperature.

The resultant product had an acid value of 36.2 mg KOHg$^{-1}$.

The utility of the emulsifiers of the above Examples in explosives compositions was demonstrated as follows.

Emulsions were prepared by the slow addition of aqueous phase (ammonium nitrate, 82.2 parts, and tap water, 12.8 parts) to oil phase (heavy liquid paraffin, 4 parts, and the emulsifier under test, 1 part) under a regime of vigorous agitation at about 95° C.

After preparation the test emulsions so produced were transferred to small (about 60 ml) storage jars and centrifuged for 1 minute at 3000 rpm whilst still warm to expel any large air bubbles.

The emulsion samples were then stored at ambient temperature 20°–25° C.) and inspected at intervals for signs of degradation ("splitting" of oil/water phases and/or crystallisation of the aqueous phase).

The following table records the time taken for significant degradation to be observed.

| Emulsifier | Degradation time/days |
| --- | --- |
| Example 4 | ≈–124 |
| Example 5 | >1500 |
| Example 6 | >1500 |
| Example 7 | >1500 |
| Example 8 | >1500 |
| Sorbitan monooleate (comparative example) | 80–100 (typical values) |

The emulsifiers of the invention were found to allow the preparation of good quality inverse emulsions, exhibiting stability better than, and in some cases far better than, that of sorbitan mono-oleate, a well known emulsifier for inverse systems.

We claim:
1. The method of incorporating a γ-lactone of formula:

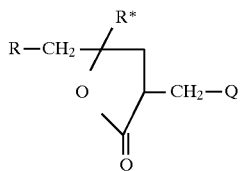

or a δ-lactone of formula:

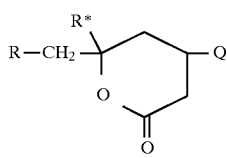

as an emulsifier in an explosive composition, wherein R is a hydrocarbyl group: R* is hydrogen, methyl or another hydrocarbyl group, which may be the same as or different from R; and Q is (i)

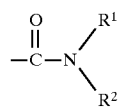

wherein $R^1$ is hydrogen or an alkyl, cycloalkyl or aryl group which may optionally be substituted: and $R^2$ is hydrogen or an alkyl, cycloalkyl or aryl group which may optionally be substituted;

(ii)

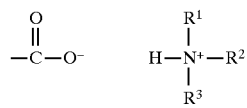

where $R^1$ and $R^2$ are as defined above and $R^3$ is hydrogen or an alkyl, cycloalkyl or aryl group which may optionally be substituted; or (iii)

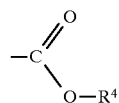

where $R^4$ is a hydrocarbyl or substituted hydrocarbyl group derived from an alcohol, monomeric polyol or oligomeric poly(oxyalkylene) or alkanolamine.

2. The method according to claim 1, wherein R is a saturated poly(alkylene) group, where the alkylene part has from 2 to 6 carbon atoms.

3. The method according to claim 2, wherein R is a saturated polyisobutylene group of the formula:

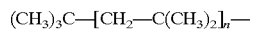

where n is from 5 to 120.

4. The method according to claim 3, where n is from 10 to 60.

5. An explosive composition comprising an emulsion having an organic continuous phase and a discontinuous aqueous phase containing an oxygen-supplying compound and a γ-lactone of formula:

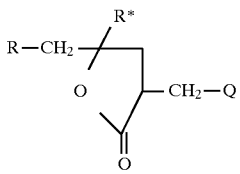

or a δ-lactone of formula:

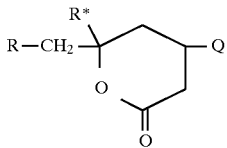

wherein R, R* and Q are as defined in claim 1.

6. A composition according to claim 5, wherein R is a saturated poly(alkylene) group, where the alkylene part has from 2 to 6 carbon atoms.

7. A composition according to claim 6, wherein R is a saturated polyisobutylene group of the formula:

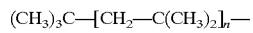

where n is from 5 to 120.

8. A composition according to claim 5, wherein the organic, continuous phase is selected from fuel oils, diesel oil, gasoline, kerosene, naptha, paraffin oils, waxes, animal oils, fish oils, methyl and/or ethyl esters of fatty acids (biodiesels) and other mineral, hydrocarbon or fatty oils, and any mixture of two or more thereof.

9. A composition according to claim 8, wherein the organic continuous phase is a liquid hydrocarbon.

10. A composition according to claim 5, wherein the oxygen-supplying compound is selected from alkali and alkaline earth metal nitrates, chlorates and perchlorates: ammonium nitrate, chlorates and perchlorates: and any mixture of two or more thereof.

11. A composition according to claim 10, wherein the oxygen-supplying compound is ammonium nitrate or a mixture of ammonium nitrate and sodium or calcium nitrate.

12. A composition according to claim 5, wherein the organic phase comprises 2% to 15% by weight of the composition and the aqueous phase comprises 85% to 98% by weight of the composition, the oxygen-supplying compound comprising 40% to 95% by weight of the composition and the γ-lactone or δ-lactone comprising up to 5% by weight of the composition.

* * * * *